United States Patent [19]

Fossel

[11] Patent Number: 5,366,440
[45] Date of Patent: Nov. 22, 1994

[54] METHODS FOR TREATING DISEASE STATES USING OXIDIZED LIPOPROTEINS IN CONJUNCTION WITH CHEMOTHERAPEUTIC EFFECTOR AGENTS

[75] Inventor: Eric T. Fossel, Chestnut Hill, Mass.

[73] Assignee: The Beth Israel Hospital Association, Boston, Mass.

[21] Appl. No.: 4,079

[22] Filed: Jan. 13, 1993

Related U.S. Application Data

[60] Division of Ser. No. 592,553, Oct. 4, 1990, Pat. No. 5,192,264, which is a continuation-in-part of Ser. No. 418,382, Oct. 6, 1989, abandoned.

[51] Int. Cl.$^5$ .............................................. A61M 37/00
[52] U.S. Cl. ............................................ 604/4; 604/5; 604/6; 604/51; 128/898
[58] Field of Search ....................... 604/4, 5, 6, 49, 51; 128/898

[56] References Cited

U.S. PATENT DOCUMENTS

| | | | |
|---|---|---|---|
| 2,095,388 | 10/1937 | Luther . | |
| 3,655,700 | 4/1972 | Siddall | 260/405 |
| 3,959,287 | 5/1976 | Goldstein . | |
| 4,126,416 | 11/1978 | Sears | 23/230 B |
| 4,226,713 | 10/1980 | Goldberg | 23/230 B |
| 4,472,303 | 9/1984 | Tanihara | 260/112 B |
| 4,544,630 | 10/1985 | Ziegenhorn et al. | 435/11 |
| 4,608,347 | 8/1986 | Bernstam | 436/175 |
| 4,912,092 | 3/1990 | Gruber | 514/45 |
| 4,933,844 | 6/1990 | Otvos . | |
| 4,940,055 | 7/1990 | Brown | 128/653 A |
| 5,122,112 | 6/1992 | Jones | 604/4 |
| 5,192,264 | 3/1993 | Fossel | 604/4 |
| 5,217,716 | 6/1993 | Fossel et al. | 424/94.4 |

OTHER PUBLICATIONS

Bell et al., "'H NMR Studies of human blood plasma," 219, FEB Letters, No. 1, 239–243 (Jul. 1987).
Dixon et al., Enzymes, 740–741, Academic Press, New York (1979).
Hessler et al., "Lipoprotein oxidation and . . . ," 3(3), Arteriosclerosis, 215–222 (1983).
Hore et al., "Solvent Suppression in Fortran . . . ," 55, J. of Mag. Res., 283–300 (1983).
Morel et al., "Low density lipoprotein cytotoxicity . . . ," 24, J. of Lipid Research, 1070 (1983).
Science News, Apr. 14, 236 (1990).
Shulman et al., "NMR–Another Cancer . . . ," 322(14), New England J. Med., 1002–3 (1990).
Wako et al., "Determination of hydrogen peroxide," 95(128864P), Chem. Abstracts (1981).
Yoshioka et al., "Lipid peroxidation and its . . . ," 97(160247), Chem. Abstracts (1982).
Christopherson, B. O., Biochem, Biophys, v. 164 (1), 35–46 and Abstract (1968).
Edelson, R., et al, N. Eng. J. of Med., v. 316, pp. 297–303, (1987), "Treatment of Cutaneous T–Cell Lymphoma by Extracorporeal Photochemotherapy".
Garner, C. W., Lipids, 19(11), 863–8 & Abstract 42042v (1984) "Peroxidation of free and esterified fatty acids by . . . ".

(List continued on next page.)

Primary Examiner—Paul Prebilic
Attorney, Agent, or Firm—Lorusso & Loud

[57] ABSTRACT

The present invention relates to treating disease states in a living patient using oxidized lipoproteins, preferably low density peroxidized lipoproteins. Methods and apparatus are provided for preparing the oxidized lipoproteins. It has been discovered that diseased cells, characterized by an increased number of lipoprotein receptors or an enhanced ability to take up lipoproteins are more susceptible than healthy cells to the the cytotoxic effect of oxidized lipoproteins. Oxidized lipoproteins are used to treat disease states such as cancer, malaria and viral infections such as acquired immunodeficiency syndrome (AIDS). Proton and carbon-13 NMR spectroscopy is used to measure the degree and effect of treatment with oxidized lipoproteins.

5 Claims, 10 Drawing Sheets

OTHER PUBLICATIONS

Hatzelmann, A., *Eur. J. Biochem*, V180(3), 527–333 & Abstract (1989), "Involvement of Glutathione Peroxidase Activity . . . ".

Lehninger, Chapter 11, *Lipids Lipoproteins & Membranes*, "Lipoprotein Systems," p. 301 (1975).

Palladino, Michael et al, *Jour. of Immunology*, v. 138, p. 4023-3 "Characterization of the Antitumor Activities of Human . . ." 1987.

Pokorny, Jan et al, *Chem. Abstracts*, vol. 78, p. 178, 39712u "Origin & structure of dimeric fatty acids" (1973).

Semb, Henrik, et al, *Jour. of Biolo. Chemistry*, v. 262, n.17 pp. 8390–8394, "Multiple Effect of TNF", Jun. 15, 1987.

Stryer, Lubert, W. H. Freemand & Co., N.Y., 3rd Edition, 1975 and 1988, pp. 560–564.

Chisolm, Guy, et al., "Lipoprotein Oxidation and Cytotoxicity: Effect of Probucol on Streptozotocin-Treated Rats," (1988), pp. 20B–26B.

Kita, T., et al., "The Role of Oxidized Low Density Lipoprotein in the Pathogenesis of Atherosclerosis," Aug. 1990, pp. 122–127.

Kosugi, K., et al., "Toxicity of Oxidized Low-Density Lipoprotein to Cultured Fibroblasts is Selective for S Phase of the Cell Cycle," J. of Cellular Physiology, pp. 311–320 (1987).

Hamilton, T., et al., "Oxidized Low Density Lipoprotein Suppresses the Expression of Tumor Necrosis Factor-mRNA in Stimulated Murine Peritoneal Macrophages," (1990) J. of Immumology, pp. 2343–2350.

METHODS FOR TREATING DISEASE STATES USING OXIDIZED LIPOPROTEINS IN CONJUNCTION WITH CHEMOTHERAPEUTIC EFFECTOR AGENTS

STATEMENT REGARDING FEDERALLY SPONSORED RESEARCH

Funding for work described herein was provided by the Federal Government under a grant from the Department of Health and Human Services. The Government may have certain rights in this invention.

CROSS-REFERENCE TO RELATED APPLICATION

This application is a divisional of U.S. patent application Ser. No. 07/592,553 filed Oct. 4, 1990, which issued as U.S. Pat. No. 5,192,264 on Mar. 9, 1993 and which was in turn a continuation-in-part of U.S. patent application Ser. No. 07/418,382 filed Oct. 6, 1989, now abandoned.

BACKGROUND OF THE INVENTION

1. Field of the Invention

This invention relates to treating disease states in a living patient using oxidized lipoproteins, preferably peroxidized low density lipoproteins (p-LDL). More particularly, it relates to a method for increasing the quantity of oxidized or peroxidized lipoproteins, which includes chylomicrons, chylomicron remnants, very low density lipoproteins, intermediate density lipoproteins, low density lipoproteins and high density lipoproteins; taken up by diseased cells. All of these can serve as a source of oxidized lipoprotein. It also relates to a method and an apparatus for producing and administering effective doses of oxidized lipoproteins into a patient's bloodstream. The invention also relates to novel classes of oxidized lipoproteins which can be used to treat disease states.

2. Prior Art

It is possible to distinguish between people with cancer and healthy individuals without cancer on the basis of H-1 and C-13 NMR spectra. Methods and apparatuses for such diagnosis are described in the following patents issued to Eric T. Fossel the teachings of which are incorporated herein by reference: "Process for the Screening of Cancer Using Nuclear Magnetic Resonance"; U.S. Pat. No. 4,912,050, Mar. 27, 1990 and "Process for the Detection of Cancer Using NMR"; U.S. Pat. No. 4,918,021, Apr. 17, 1990.

In accordance with the aforementioned inventions, it was discovered that the majority of resonances in the non-water H-1 signals and the resonances of the C-13 nuclear magnetic resonance (NMR) spectra of fluid samples from both normal and cancerous patients arise from lipids and small molecules. It was found that comparing the full linewidths at half-height of the water-suppressed proton spectra with standard values provides a statistically reliable cancer diagnosis. In particular, comparing the average full linewidths at half-height of the methyl and methylene group resonance lines with a standard value of 33 Hz provides a basis for classifying persons into classes; with and without cancer. Average values below 33 Hz are taken as indicating the presence of malignancy.

It was further discovered that the major source of error in such diagnoses was hypertriglyceridemia. A method was developed to overcome this difficulty in diagnosis. It was found that C-13 spectra provide a further basis for classifying persons with high triglyceride levels (above 190 mg/dl) into two groups; cancerous or non-cancerous. The sample used to generate the H-1 NMR spectrum can be used to generate a C-13 NMR spectrum. The olefinic region of the spectrum is diagnostic. A ratio of the signal at 128 ppm of resonance frequency to that at 130 ppm was obtained. A ratio of greater than 0.9 indicates that the initial characterization from the proton NMR diagnosis was a false positive. However, a 128/130 ratio of less than 0.9 confirms the positive diagnosis. A complete evaluation comprising analysis of both H-1 and C-13 NMR spectra is more accurate than the proton test alone.

The resonance peak at 128 ppm is due to linoleic acid, an eighteen carbon polyunsaturated fatty acid with two double bonds. It must be supplied via ones' diet as the body cannot synthesize such fatty acids. The resonance peak at 130 ppm is due both to polyunsaturated fatty acids such as linoleic acid and monounsaturated fatty acids such as oleic acid, an eighteen carbon fatty acid produced by the body. The relative height of these peaks is affected by the cancerous state of the patient. Persons with untreated cancer have low levels of linoleic acid in their bodies. This is caused by the oxidation of unsaturated fatty acid chains with linoleic acid being more rapidly peroxidized by hydroxyl free-radicals. Since linoleic acid contains a double bond pair capable of delocalizing an electron when in the radical state, its radical intermediate has a lower free energy than the oleic acid radical. Free-radical induced oxidation therefore results in a decreased proportion of polyunsaturated fatty acids such as linoleic to monounsaturated fatty acids such as oleic acid and consequently of the resonance peak at 128 ppm relative to that at 130 ppm.

Linoleic acid is a constituent of triglycerides, cholesterol esters and phospholipids which are components of low density lipoproteins (LDL), the major carrier of cholesterol in the blood. Much of the cholesterol carried by LDL is esterified, principally to linoleic acid. In addition, LDL is made up of phospholipids and a large core protein of 514 kD, protein B-100. All together, LDL is about 22 nm in diameter and has a mass of approximately 3 million daltons. LDL carries cholesterol to peripheral tissues. LDL receptors in coated pits on cell membranes bind protein B-100 and internalize the LDL particles. LDL is broken down inside the cell, and the LDL receptor is returned to the cell membrane. The cholesterol may be incorporated into the cell membrane or stored in the cell in esterified form. Cells which have enough cholesterol stop producing LDL receptors which have a lifespan of about one day. A more detailed discussion of this and related mechanisms can be found in Stryer, *Biochemistry*, W. H. Freeman and Company, New York, 1988, pp. 560 ff. The foregoing method for detecting cancer has enabled the monitoring of cell components that are diagnostic for cancer. This screening technique has enabled the present discovery by providing insight into the mechanism of action of the present invention.

It was separately known that the cytokine tumor necrosis factor (TNF), a 17 kD protein, has a number of effects, including in vitro and in vivo tumor cell necrosis. TNF is released from macrophages in response to malignant cells. Nathan, *J. Clin. Inves.*, 1987, vol. 79, pp. 319-26. TNF then causes alteration of plasma lipoprotein lipids by suppressing lipoprotein lipase activity.

Beutler et al., *J. Exp. Med.*, 1985, vol. 161, p. 984; Semb et al., *J. Biolog. Chem.*, 1987, vol. 262, pp. 8390–94. It also induces polymorphonuclear neutrophils (PMN) to undergo a respiratory burst resulting in lipid peroxidation. Figari et al., *Blood*, 1987, vol. 70, 979–84.

In addition to its production in response to cancer, TNF is released in response to a variety of other relatively rare and easily definable disease states including malaria, gram negative endotoxin shock, uncontrolled diabetes, AIDS, and organ rejection. Since the 1980's, when TNF-like activities were first described, several TNFs have been isolated and characterized. TNF-a, the original TNF, is the TNF referred to in this application.

The list of activities attributed to TNF is growing rapidly. It has been found to have a wide range of biological activities in addition to anti-tumor activity. These include inhibiting lipoprotein lipase activity (Beutler et al, supra; Semb et al., supra), inhibiting bone marrow differentiation (Degliantoni et al., *J. Exp. Med.*, 1985, vol. 162, p. 1512), and interacting with the regulation of producing other cytokines and their receptors (Dinarello et al, *J. Exp. Med.* 1986, Vol. 163, p. 1433). Despite its many effects, the mechanism by which TNF exhibits its anti-tumor effect remains a subject of debate.

An important step toward understanding the mechanism was taken in a series of experiments with Meth A sarcoma cells by Palladino et al. *J. Immunol.*, 1987, Vol. 138, pp. 4023–32. They suggested that TNF does not directly assert its anti-tumor effect on Meth A sarcoma cells, but rather requires the mediation of other cells or substances. Recent reports by Palladino implicate polymorphonuclear neutrophils (PMN) as mediators. Figari et al., supra. It was shown that TNF (and, to a much lesser extent, other cytokines) stimulates a respiratory burst in PMN resulting in production of superoxide, $O_2^-$. Superoxide is a precursor to hydroxyl radicals (·OH), a highly reactive species which oxidizes many tissue constituents.

It is known that cytotoxicity is associated with oxidized lipids. Peroxide itself is toxic to virtually all cell types. More recently, several workers have focused attention on the cytotoxicity of the polyunsaturated fatty acid peroxidation products.

Unfortunately, in addition to all of its useful activities, TNF produces very toxic side effects. It has, therefore, been difficult to use TNF for fighting cancer in humans. It is desirable to find a chemotherapeutic agent which will target cancer cells preferentially.

A study by Edelson et al. *N. Eng. J. of Med.*, 1987, Vol. 316, pp. 297–303 describes treatment effective for some cutaneous lymphomas and certain leukemias whereby a photosensitizer is added to blood and the blood is irradiated with ultraviolet light. In that study, an aromatic compound, 8-methoxypsoralen, was ingested by a patient. Several hours later blood was withdrawn and irradiated with ultraviolet light (type A) and then re-infused into the patient. This study, however, does not explain the mechanism of this method of treatment, it simply indicates that it is effective against certain forms of cancer.

The present invention provides several methods for oxidizing lipoproteins for the purpose of treating disease states and photoperoxidation is one of these methods. It is believed, that by adding a photosensitizer such as 8-methoxypsoralen to blood and then irradiating the blood with ultraviolet light, radical intermediates may be produced resulting in generation of hydroxyl radicals. It is believed that these hydroxyl radicals in turn oxidize lipoproteins.

SUMMARY OF THE INVENTION

In accordance with the present invention, it was discovered that diseased cells with an increased number of lipoprotein receptors or an enhanced ability to take up lipoproteins are more susceptible than healthy cells to the cytotoxic effect of oxidized lipoproteins as defined herein. One important method for treating diseased states characterized by diseased cells with an increased number of lipoprotein receptors, or an enhanced ability to take up lipoproteins, with peroxidized lipoproteins involves administering p-LDL directly to the patient. Such administration may be accomplished by introducing p-LDL enriched blood directly into a patient's blood stream.

Organic peroxides are capable of generating free-radicals which in turn can peroxidize LDL to fight disease states characterized by diseased cells with an increased number of lipoprotein receptors or an enhanced ability to take up lipoproteins, such as cancer, malaria and viral infections such as acquired immunodeficiency syndrome (AIDS). Thus, a second method for treating such disease states using oxidized lipoproteins comprises introducing a therapeutic dose of organic peroxide into a diseased patient together with a chemotherapeutic effector agent, such as taurine or lovastatin, which makes p-LDL more cytotoxic to diseased cells, by further increasing the number of lipoprotein receptors on a diseased cell or by increasing the rate of uptake of the cell for lipoproteins. Administering non-oxidized but modified LDL should enhance the effect of the organic peroxides. Modified LDL are prepared by enriching the content of natural LDL with specific triglycerides, phospholipids, or cholesterol esters which are more easily oxidized or which result in more cytotoxic peroxidation products.

A third method for producing peroxidized lipoproteins involves subjecting blood fluid lipids directly to hydrogen peroxide alone or in tile presence of an enzyme such as peroxidase. An apparatus for accomplishing the latter method is described which comprises an extracorporeal module for installation in an AV (atrio-ventricular) shunt or arterial bypass, which includes a peroxidizing module and an inlet from a means such as a pump which can slowly and precisely introduce a flow of peroxide. The latter method may additionally comprise adding a chemical effector agent as well. Utilizing blood as a source of oxidized low density lipoproteins is a very important embodiment of the present invention. This embodiment has many variations.

For example, in its simplest embodiment, blood is removed from a patient and treated under peroxidizing conditions to oxidize or peroxidize the lipoproteins present in the blood. The blood can be monitored for oxidized lipoprotein level by proton and carbon-13 NMR and returned to the patient where the oxidized lipoproteins will come in contact with high metabolism diseased cells, such as cancer cells, where the peroxidized lipoprotein will be taken up by such cells and the cell will be killed. In addition to this method, a patient's blood, or for that matter, blood from a donor source, can be treated as described above, but in addition, the blood can be enriched with lipoproteins from other sources and then oxidized. Furthermore, an agent known to increase a cell's uptake of lipoproteins can be administered to the patient as a pretreatment in addition to further enriching the blood with a peroxide. Thus, in the latter embodiment, a patient can receive blood from a donor which is superenriched with oxidized lipoproteins, and which contains an agent to increase the diseased cell's ability to take up such lipoproteins, and which further contains an oxidant to oxidize those lipoproteins already present in the patient.

The lipid oxidation processes of the body may be further augmented by increasing the oxygen level in the blood via inhalation of increased levels of oxygen during breathing. Perflurocarbon fluosal may also be used to increase the oxygen level in the blood.

Accordingly, it is an object of the present invention to provide a chemotherapeutic method of acceptable toxicity for fighting diseased states, such as cancer, malaria and viral infections such as AIDS which are characterized by diseased cells with an increased number of lipoprotein receptors or an enhanced ability to take-up lipoprotein.

It is a further object of the present invention to take advantage of and boost the patient's own biological response to help the patient fight diseased states, such as cancer, malaria and viral infections such as AIDS which are characterized by diseased cells with an increased number of lipoprotein receptors or an enhanced ability to take up lipoprotein by increasing the level of oxidized lipoprotein taken up by diseased cells.

It is another object of the present invention to use p-LDL whose presence can be easily monitored using nuclear magnetic resonance spectroscopy to fight cancer, malaria and viral infections such as AIDS in a patient.

It is yet another object of the present invention to provide a chemotherapeutic method which will fight all forms of cancer.

It is a still further object of the present invention to provide a method and an apparatus for peroxidizing lipoproteins in the blood of a patient to produce a source of p-LDL.

Other objects and advantages of the invention will become apparent from the description of the invention which follows made with reference to the drawings below.

DESCRIPTION OF THE PREFERRED EMBODIMENTS

Figure 1A:
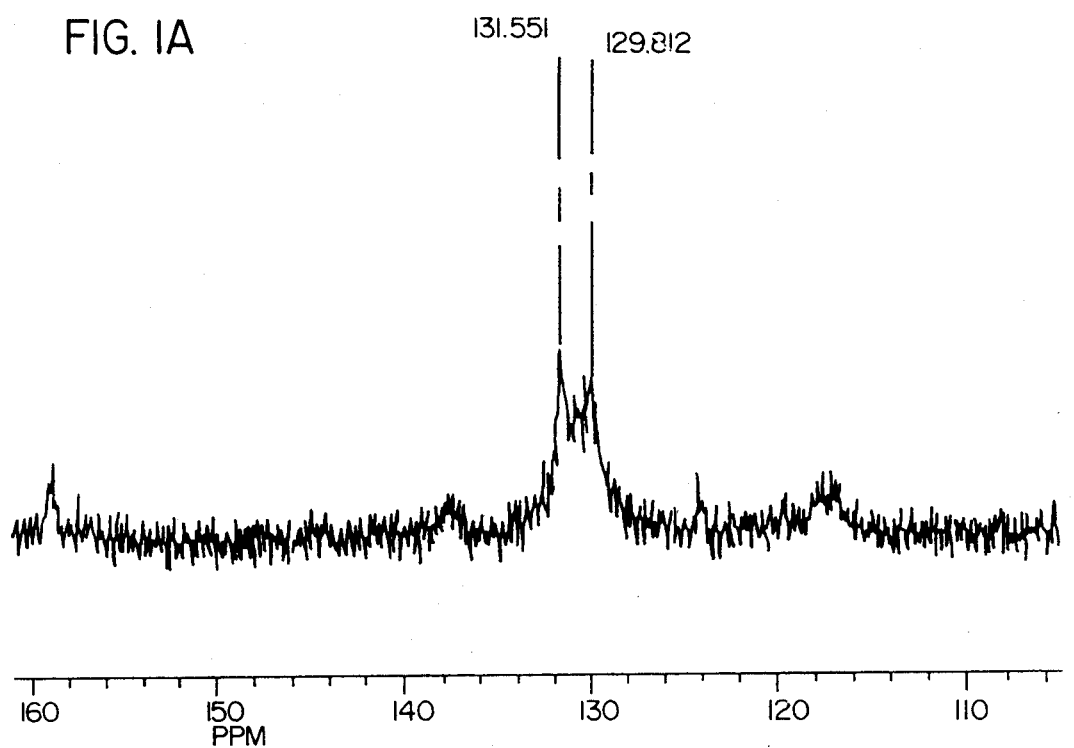
FIG. 1A shows the olefinic region of a C-13 spectrum of a normal human plasma sample.

At the outset, the invention is described in its broadest overall aspects, with a more detailed description following. In its broadest overall aspects, the invention is a method of treating a disease state characterized by the presence of diseased cells with an increased number of lipoprotein receptors or an enhanced ability to take up lipoproteins by absorbing an oxidized lipoprotein, preferably a peroxidized low density lipoprotein, to the diseased cells. In accordance with the present invention, it has been discovered that oxidized or peroxidized lipoproteins will preferentially kill diseased cells. It is also known that cells present in many diseased states, such as cancer, malaria and viral infections such as AIDS have a number of lipoprotein receptors over and above that which would normally be expected for a particular cell or they exhibit an enhanced ability to take-up lipoproteins. Examples of viruses and virus infections that may be treated by the administration of oxidized lipoproteins include retroviruses including HIV, hepatitis, cytomegalovirus, herpes, pneumonia, varicella zooster virus, influenza virus and others.

The likely reason for the increased number of receptors is that these cells have a large appetite and thus require fuel. Lipids in the lipoproteins are fuel in accordance with the present invention, it has been discovered that cells with lipoprotein receptors can be destroyed by oxidized lipoproteins. The present invention is directed to the many different ways to increase the likelihood that oxidized lipoproteins will be taken up by diseased cells and destroy them.

As part of its response to diseases such as cancer, malaria and viral infections such as AIDS, a human host oxidizes lipoproteins circulating in the blood. Lipoproteins take various forms in the blood including chylomicrons, chylomicron remnants, very low density lipoproteins, intermediate density lipoproteins, low density lipoproteins, and high density lipoproteins. Certain lipids associate with specific proteins to form lipid:protein systems in which the specific physical properties of these two classes of biomolecules are blended. There are two major types, transport lipoproteins and membrane systems. In these systems, the lipids and proteins are not covalently joined but are held together largely by hydrophobic interactions between the nonpolar portions of the lipid and the protein components. The plasma lipoproteins are complexes in which the lipids and proteins occur in a relatively fixed ratio. They carry water-insoluble lipids between various organs via the blood, in a form with a relatively small and constant particle diameter and weight. Human plasma lipoproteins occur in four major classes that differ in density as well as particle size as shown in the table below.

| Major Classes of Human Plasma Lipoproteins | | | | |
|---|---|---|---|---|
| | Chylomicrons | Very low density lipoproteins (VLDL) | Low-density lipoproteins (LDL) | High-density lipoproteins (HDL) |
| Density, g ml$^{-1}$ | <0.94 | 0.94–1.006 | 1.006–1.063 | 1.063–1.21 |
| Flotation rate, $S_f$ | >400 | 20–400 | 0–20 | (Sediment) |
| Particle size, nm | 75–1,000 | 30–80 | 20–22 | 7.5–10 |
| Protein, % of dry weight | 1–2 | 10 | 25 | 45–55 |
| Triocylglycerols, % of dry weight | 80–95 | 55–85 | 10 | 3 |
| Phospholipids, % of dry weight | 3–6 | 15–20 | 22 | 30 |
| Cholesterol, free, % of dry weight | 1–3 | 10 | 8 | 3 |
| Cholesterol, esterified, % of dry weight | 2–4 | 5 | 37 | 15 |

There are pathways within the body for interconversion among the four major classes. Thus, any of the four classes can be administered but it is the peroxidized low density lipoproteins that are most effective.

As shown in the above table, the plasma lipoproteins contain varying proportions of protein and different types of lipid. The very low-density lipoproteins contain four different types of polypeptide chains having distinctive amino acid sequences. The high-density lipoproteins have two different types of polypeptide chains, of molecular weight 17,500 and 28,000. The polypeptide chains of the plasma lipoproteins are believed to be arranged on the surface of the molecules, thus conferring hydrophilic properties. However, in the very low-density lipoproteins and chylomicrons, there is insufficient protein to cover the surface; presumably the polar heads of the phospholipid components also contribute hydrophilic groups on the surface, with the nonpolar triacylglycerols in the interior. *Biochemistry*, Lehninger, Worth Publishers, Inc., New York, 1975, pp. 301.

When low density lipoproteins (LDL) are oxidized, they have a cytotoxic effect which preferentially kills diseased cells which have an enhanced ability to take-up lipoproteins.

An important factor in selecting a lipoprotein for killing diseased cells according to tile present invention is that the lipoprotein chosen be one which the diseased cells have an enhanced ability to take-up, or transport across their membrane. Another important characteristic of the lipoprotein is that it be capable of being oxidized, preferably peroxidized by reaction with hydrogen peroxide. However, in all embodiments described herein, LDL, HDL and VLDL may be oxidized for the purpose of treatment of disease states. Also, in all embodiments described herein where lipoproteins present in bodily fluids are oxidized, whole blood, plasma and serum may be used in accordance with the present invention.

Although it is believed that the oxidation of lipoproteins according to the present invention produces a new class of substances, tile chemistry for oxidizing lipoproteins is readily apparent from analyzing the prior art. In this regard, the procedures and techniques for oxidizing lipids are well documented. According to the most preferred embodiment of the present invention lipoproteins are oxidized by reaction with horseradish peroxidase and hydrogen peroxide.

In accordance with tile present invention one method for treating disease states, such as cancer, malaria and vital infections such as AIDS which are characterized by diseased cells with an increased number of lipoprotein receptors or an enhanced ability to take-up lipoproteins, using p-LDL is as follows. Therapeutic doses of an oxidant, such as an organic peroxide, or more specifically such as ditertiarybutyl peroxide are introduced into patients diagnosed as having cancer or malaria or AIDS by methods well known in the art. The progress of the disease is monitored by conventional methods and the organic peroxide dose adjusted accordingly. Administering modified lipoproteins should enhance the effect of these peroxides. Modified lipoproteins are prepared by enriching the content of natural lipoproteins with specific triglycerides such as trilinoleal triglyceride, phospholipids such as dilinoleal phosphatidylcholine, or cholesterol esters such as cholesterol ester of linoleic acid. Other enzymes and oxidants such as flavins and riboflavin; oxidases such as peroxidase and lipoxidase may also be used per this embodiment.

Figure 6:
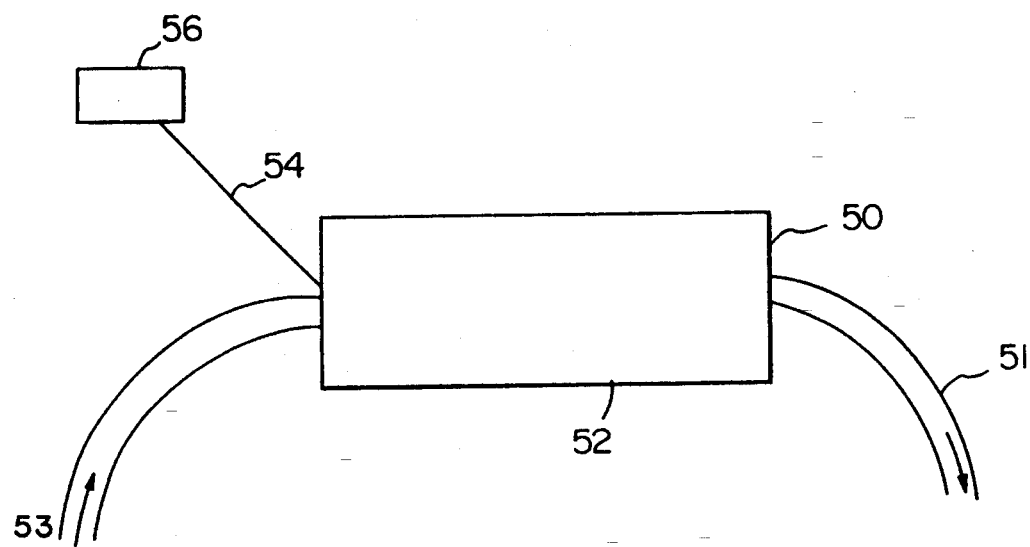
FIG. 6 shows the apparatus of the invention.

FIG. 6 illustrates the second embodiment where the lipoproteins in a patient's blood are peroxidized directly by the method and apparatus of the invention. The apparatus consists of an extracorporeal peroxidizing module 50 which is installed through an A-V shunt or arterial bypass. The module 50 includes an immobilized enzyme 52 such as peroxidase or lipoxidase and an inlet 54 from a pump 56 which can very slowly and precisely introduce a flow of hydrogen peroxide into the blood. Blood 53 from the patient's artery enters the module and returns to the patient's vein via 51.

Both methods of the invention may also include using additional chemical effector agents. Taurine ($NH_2CH_2CH_2SO_3H$/ethanolaminesulfonic acid) or one of the drugs used for reducing cholesterol, such as lovastatin (MEVACOR ® $C_{24}H_{36}O_5$,[1S-[1,3,7,8,8a]]-1,2,3,7,8,8a-hexahydro-3, 7-dimethyl-8-[2-(tetrahydro-4-hydroxy-6-oxo-2H-pyran-2-yl) ethyl]-1-napthalenyl 2-methylbutanoate) may be introduced. Such drugs function by increasing the number of lipoprotein receptors on the cell membrane in a known fashion. Increasing the number of lipoprotein receptors increases the lipoprotein intake. Of course, the p-LDL particles are taken up by normal cells as well, but normal cells have a higher tolerance, presumably due to the lower rate of uptake. In the case of cancer, malignant cells are constantly growing, dividing, and synthesizing new membranes and therefore have a much greater intake of LDL. Thus, p-LDL particles are taken into malignant cells in greater numbers, where they have a cytotoxic effect.

The lipid peroxidation process of the body may be further augmented by increasing the oxygen level in the blood via inhalation of increased levels of oxygen during breathing. Perflurocarbon fluosal may also be used to increase the oxygen level in the blood.

In a third embodiment, patients with disease states characterized by diseased cells with an increased number of lipoprotein receptors are treated by direct administration of peroxidized lipoproteins. Peroxidized low density lipoproteins produce the best results. This treatment may be further supplemented by administering a chemotherapeutic effector agent, such as taurine or lovastatin, to further increase the number of lipoprotein receptors on the diseased cells.

Figure 8:
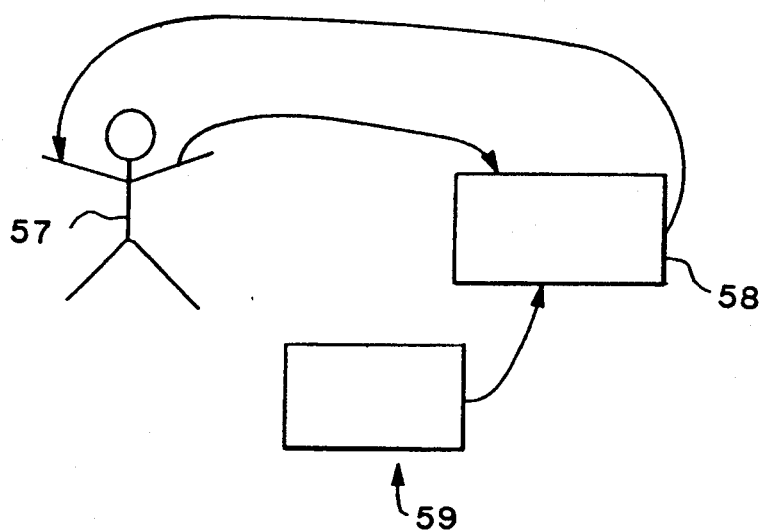
FIG. 8 shows a procedure and apparatus for oxidizing the lipoproteins of a patient.

FIG. 8 depicts another embodiment of this invention in which blood is transferred from a patient 57 to a container 58 the interior walls of which are coated with an immobilized enzyme, such as a lipoxidase, or a peroxidase such as horseradish peroxidase. A peroxide 59 is added to the container resulting in the formation of oxidized lipoproteins which are then transferred back to the patient 57.

Figure 9:
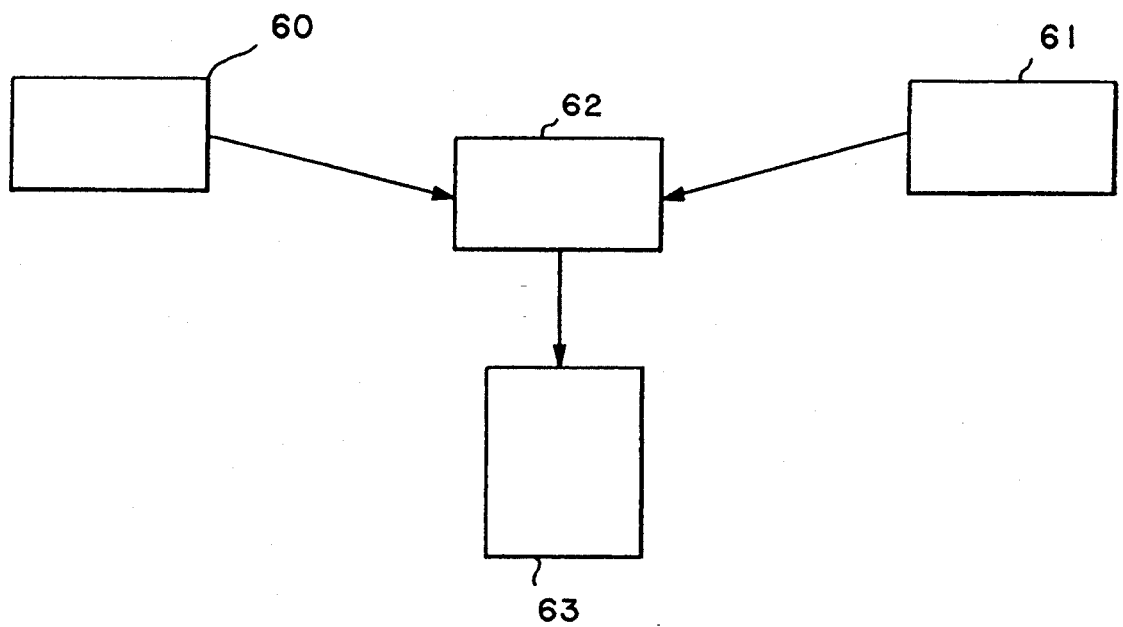
FIG. 9 shows another embodiment of the apparatus for oxidizing the lipoproteins in a blood supply.

FIG. 9 depicts still another embodiment of this invention wherein a blood supply 60 is secured. It may be from a patient, a donor or any other compatible blood source. The blood 60 and an oxidant 61, such as hydrogen peroxide, are introduced into a container 62 thus forming oxidized lipoproteins. The oxidized lipoprotein-containing blood is then transferred to a storage container 63 until needed for treatment.

Figure 7A:
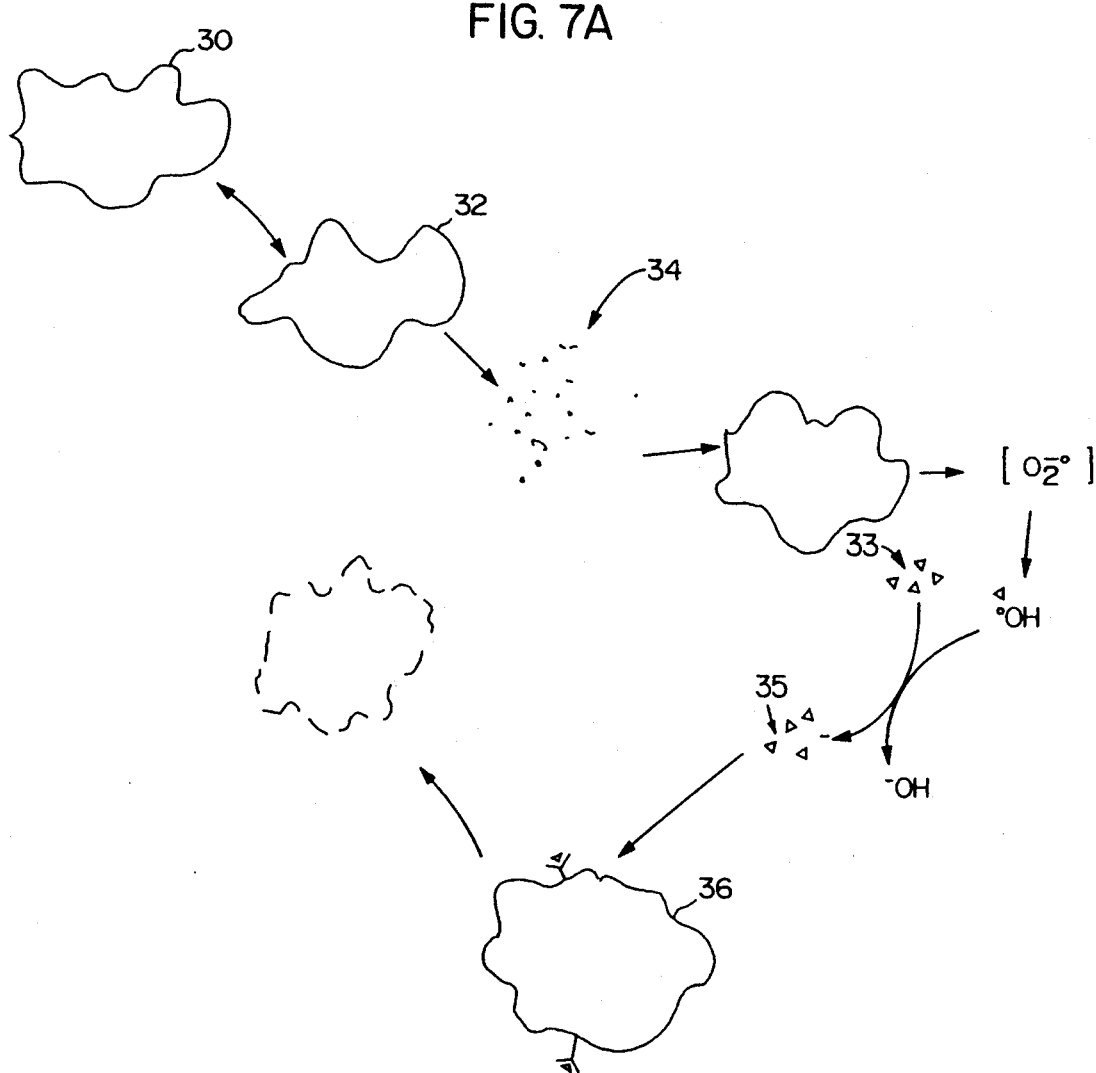
FIG. 7A is a schematic diagram of the mechanism for producing peroxidized low density lipoproteins as carried out by the human body in response to malignancy.

FIG. 7A illustrates how the cytotoxicity of p-LDL helps to fight cancer in humans. In nature, a cancer cell 30 is sensed by a macrophage 32 which secretes TNF 34. The TNF 34 induces PMN to undergo a respiratory burst to release superoxide, $O_2^-$. The superoxide causes the formation of hydroxyl free-radicals, $\cdot OH$ which in turn oxidize LDL 33 to p-LDL 35 while being converted into hydroxide ions, $^-OH$. The p-LDL 35 exert their cytotoxic effect on malignant cells 36 leading to cell death. The malignant cells 36 killed by p-LDL 35 may be the same or different than the originally sensed tumor cell 30.

Figure 7B:
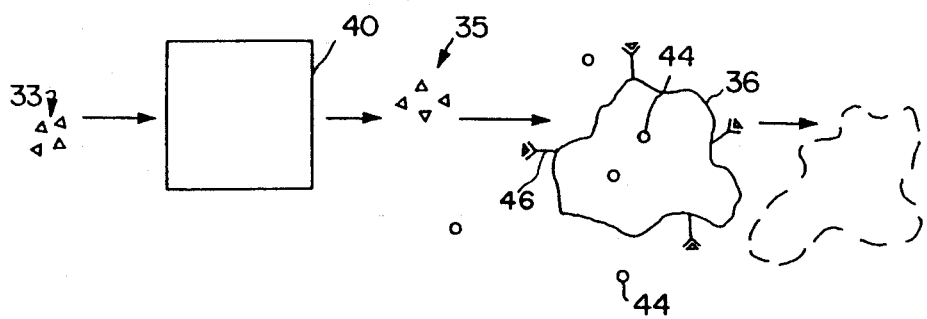
FIG. 7B is a schematic diagram of the general method for treating cancer in accordance with the claimed invention.

FIG. 7B illustrates the method of the present invention. Low density lipoproteins 33 will be converted directly to D-LDL by exposure to a chemical agent 40. In one embodiment, the agent 40 is ditertiarybutyl peroxide. In another embodiment, the agent 40 is peroxidase together with peroxide. A chemotherapeutic effector agent 44 induces the production of LDL receptors 46 which enhance the cytotoxic effect of p-LDL. The malignant cell 36 will die in preference to normal cells.

Figure 1B:
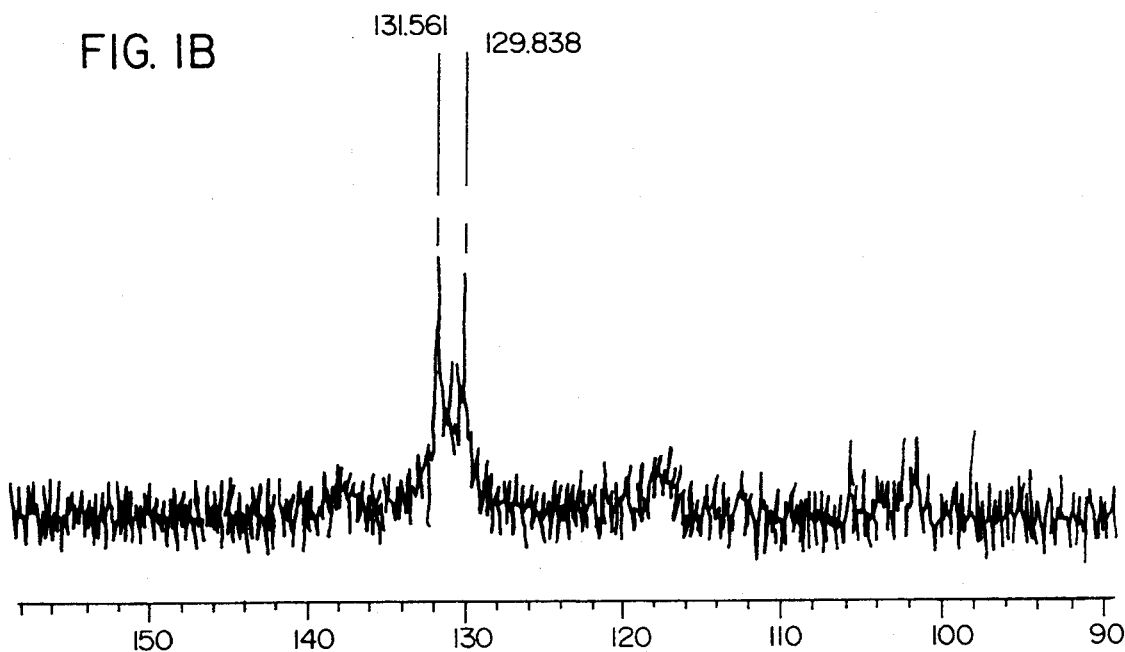
FIG. 1B shows the olefinic region of a C-13 spectrum of a human plasma sample from a person with untreated cancer.
Figure 2A:
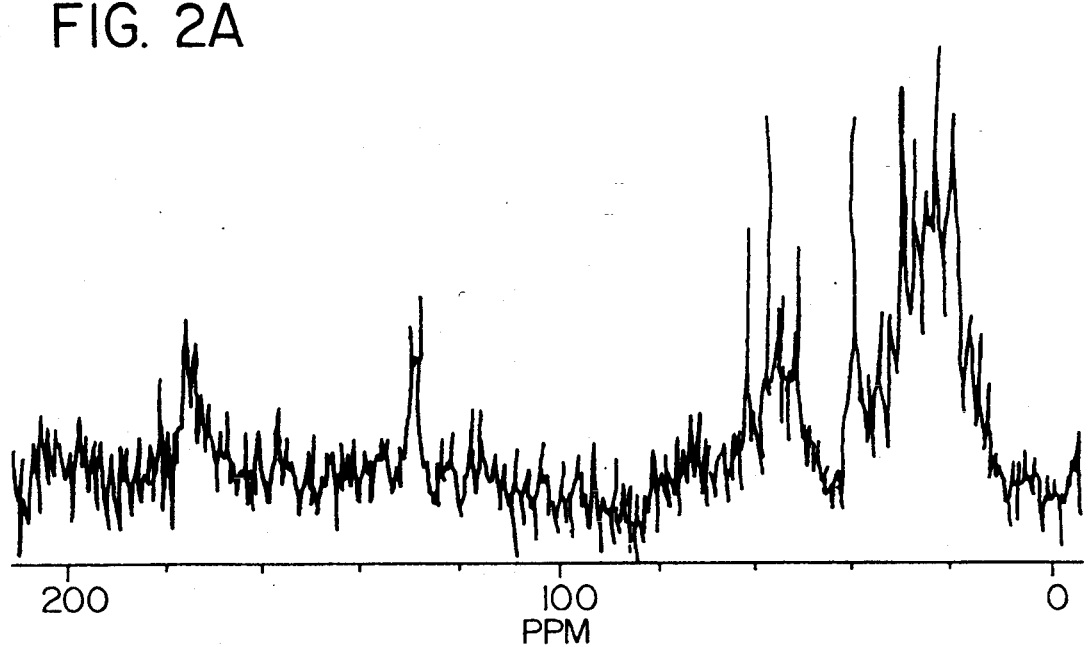
FIG. 2A shows the olefinic region of a 125.8 MHz proton decoupled spectrum from normal human plasma.
Figure 2B:
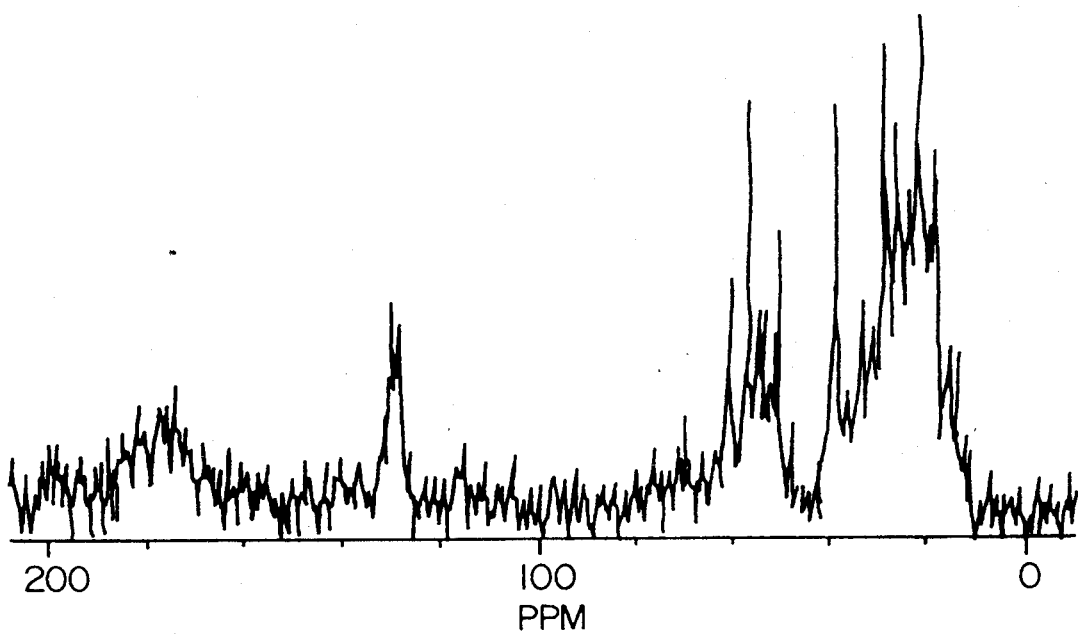
FIG. 2B shows the olefinic region of a 125.8 MHz proton decoupled spectrum of the same plasma as in FIG. 1A following the addition of peroxidase (2 mg/ml), and after 3 aliquots of 3% hydrogen peroxide (100 μl/ml) were added at hourly intervals.

FIG. 1A shows the olefinic region of a spectrum from a normal plasma sample. The ratio of the peak at 128-129 to the peak at 130-131 is near one. FIG. 1B shows the same region of a spectrum of a blood sample from a patient having untreated cancer. The ratio of the peak at 128-129 ppm of resonance frequency to the peak at 130-131 ppm is substantially less than 0.9. This decreased ratio indicates a cancerous condition, as described in U.S. Pat. No. 4,912,050. The decreased ratio is caused by the oxidation of linoleic acid, the fatty acid which produces the signal at 128 ppm. FIGS. 2A & B show the olefinic region of 125.8 MHz proton decoupled C-13 spectra from normal human plasma and the same plasma following the addition of peroxidase (2 mg/ml) and 3 aliquots of 3% hydrogen peroxide (100 μl/ml) at hourly intervals. The 128/130 ratio was substantially decreased following treatment. Thus, in vitro oxidation produces a shift in the olefinic region of the spectrum similar to that caused by the host's own response to cancer.

Figure 3A:
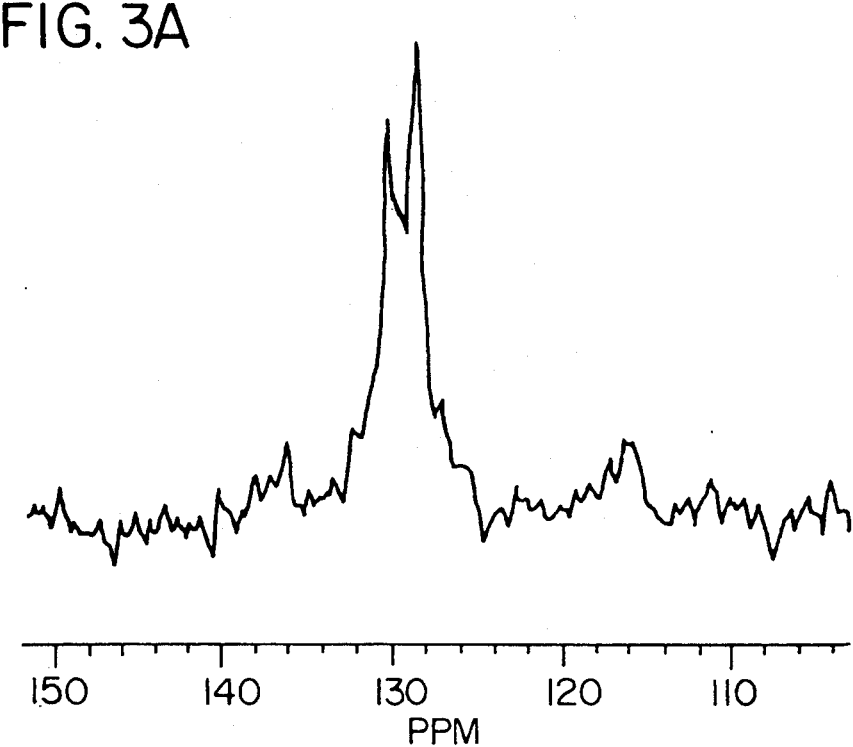
FIG. 3A shows the olefinic region of the spectrum from mouse plasma control.
Figure 3B:
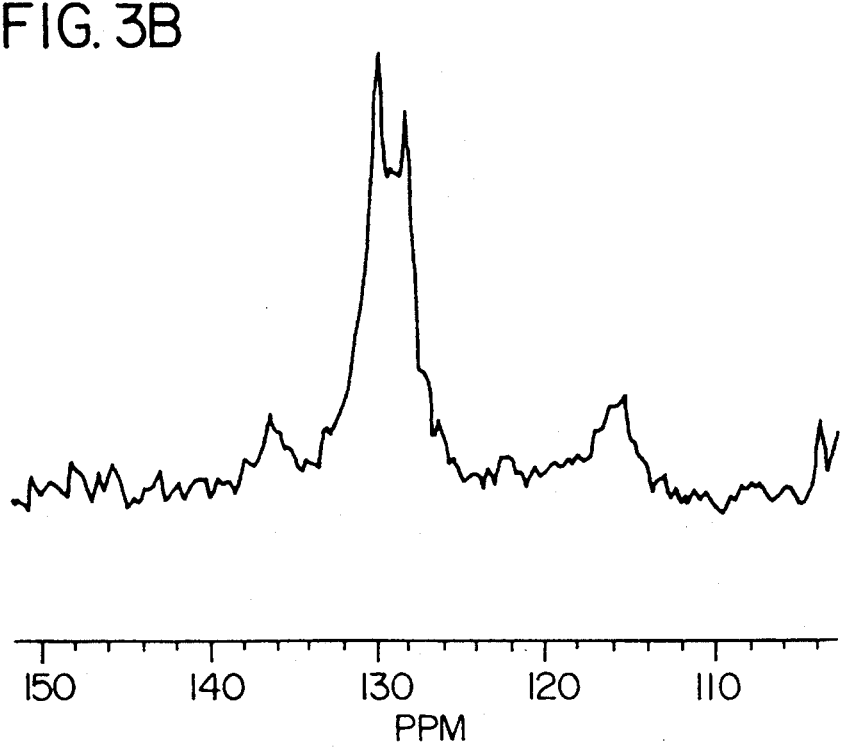
FIG. 3B shows the olefinic region of a spectrum from a mouse plasma sample treated with tumor necrosis factor.

FIGS. 3A and B show the olefinic region of a mouse plasma sample control and two hours after treatment with tumor necrosis factor (TNF), respectively. It shows the same reduced ratio (128/130) as seen in the untreated cancer and peroxidized samples. The oxidation of polyunsaturated fatty acids seen in untreated cancer occurs as a TNF-mediated host response to the malignancy.

Figure 4:
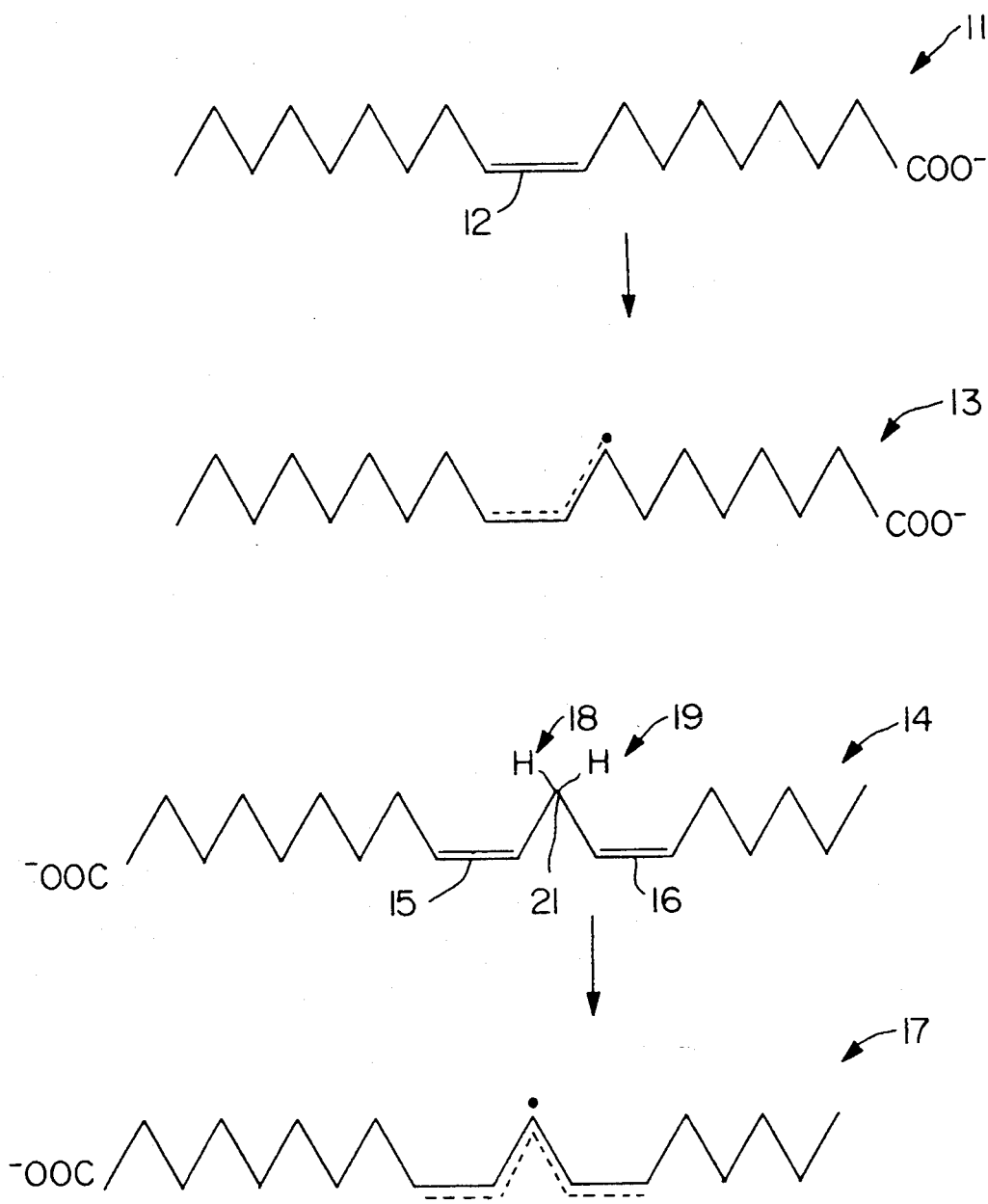
FIG. 4 shows the free radical intermediates in lipid peroxidation of mono- and diunsaturated fatty acids.

Linoleic acid is oxidized to a much greater extent than oleic acid, both by the host as a response to cancer and by peroxidase in vitro. Oleate 11, as shown in FIG. 4, contains only a single cis double bond 12. The double bond 12 serves an important role in preserving the fluidity of cell membranes, however, it is capable of only minimal stabilization of a free radical intermediate 13. Since the method of oxidation both naturally and in vitro is through hydroxyl free-radical ($\cdot OH$) induction, oleate 11 is only minimally oxidized. Linoleate 14, however, contains two unconjugated double bonds 15, 16, as shown in FIG. 4. A radical 17 is formed by removal of a proton; the easiest protons 18, 19 to remove are from the methylene group 21 between the two double bonds 15, 16. The free radical intermediate 17 is very stable, i.e. has a low free energy compared to an oleic acid-derived radical, because the lone electron is delocalized across the now conjugated double bond system. Accordingly, the reaction to produce the free radical intermediate 17 of linoleate 14 is much more thermodynamically favored and therefore much (about twenty times) faster than for oleate 11, and linoleate 14 is oxidized to a much greater degree.

In accordance with the present invention, the cytotoxic activity of peroxidized low density lipoproteins was investigated. P-LDL were prepared by treating lipoproteins with peroxide in the presence of horseradish peroxidase. Lipid peroxidation was monitored using C-13 NMR. In all experiments, one control was a solution of media containing peroxidase to which peroxide had been added, but which contained no LDL. In all instances, this control produced no effect. FIGS. 2A & B show the C-13 spectra of LDL before and after peroxide treatment, respectively. The p-LDL used had a 128/130 ratio of less than 0.8. Cytotoxicity increases with a decreasing ratio. The p-LDL were tested for cytotoxicity on a variety of malignant and non-malignant cells in culture. P-LDL kill all cells when a high enough dose is used, but malignant cells require much lower levels of p-LDL than non-malignant cells.

Figure 5A:
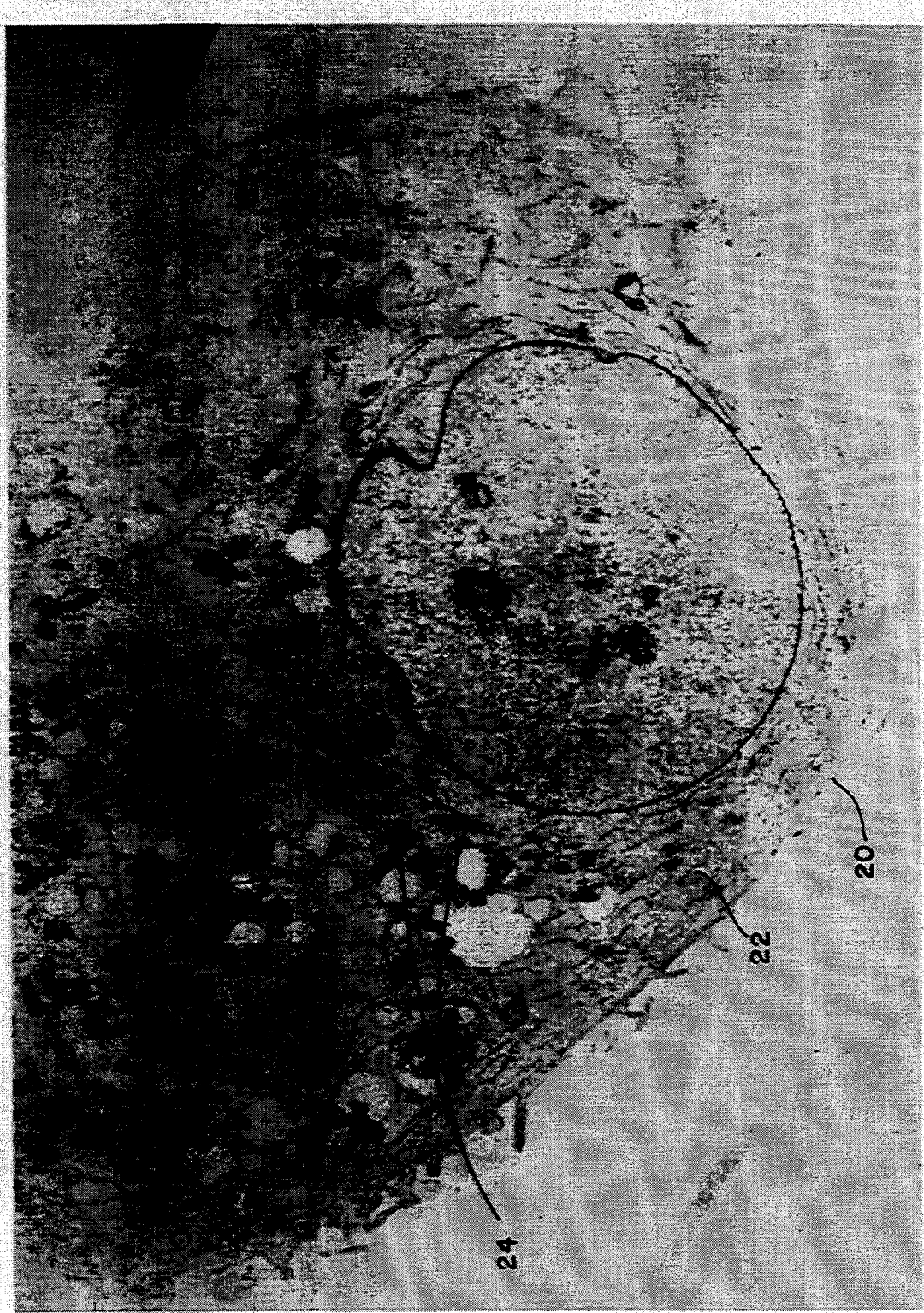
FIG. 5A shows an electron micrograph of a cultured prostate adenocarcinoma cell.
Figure 5B:
FIG. 5B shows an electron micrograph of a cultured prostate adenocarcinoma cell 1.5 hours after treatment with a 1:40 dilution of peroxidized low density lipoproteins.
Figure 5C:
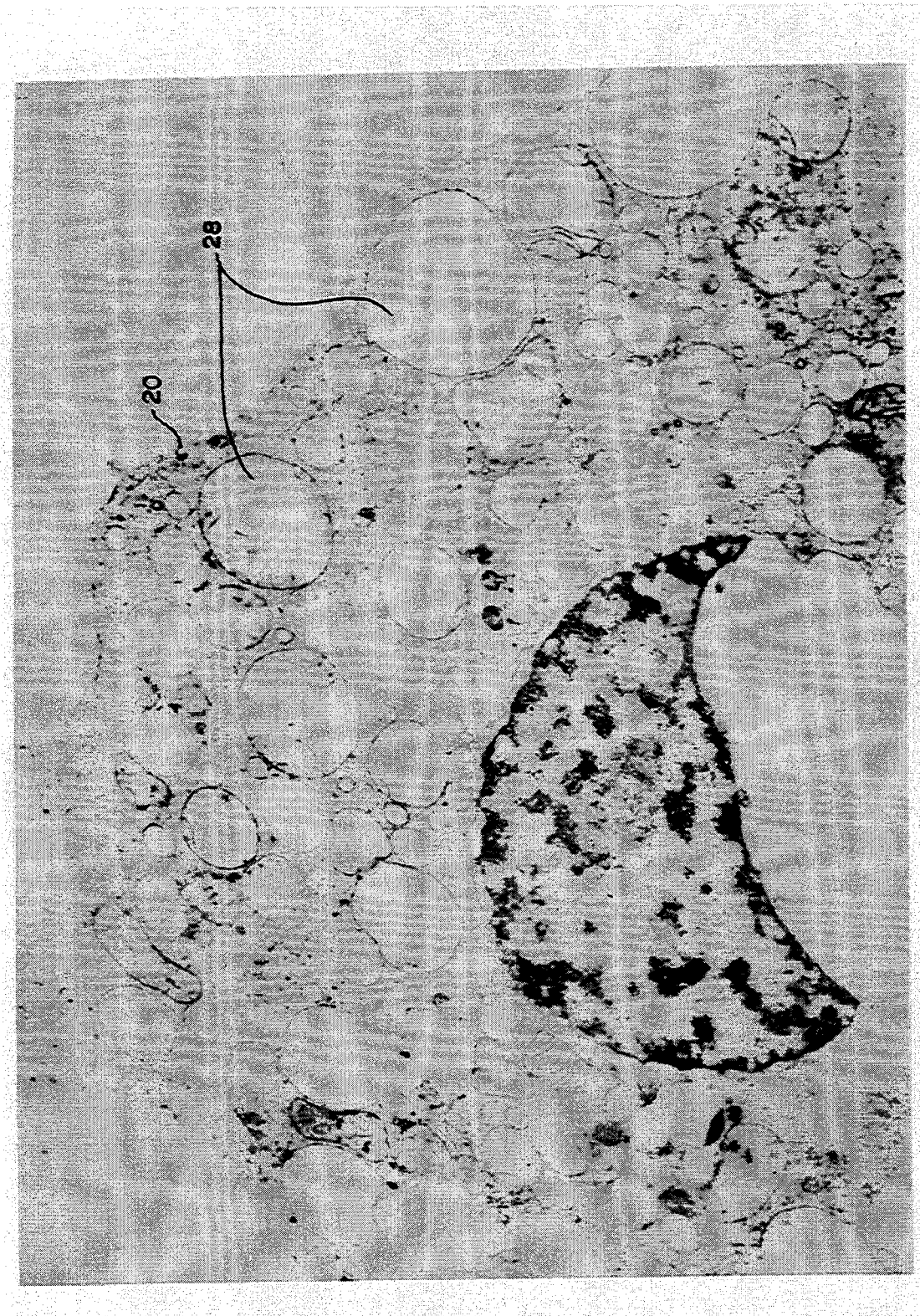
FIG. 5C shows an electron micrograph of a cell as in FIG. 5B, 4 hours after treatment.

Cell death was measured quantitatively by trypan blue exclusion and oxidation of 3-(4,5 dimethyl-thiazol-2-yl)-2,5-diphenyltetrazolium bromide (MTT). In addition, some cells were photographed by both light and electron microscopy. Cells which were tested include PC3 and DU145, both prostate adenocarcinoma cells. FIG. 5A shows an electron micrograph of a control prostate adenocarcinoma cell 20. The cytoplasm 22 looks normal and the mitochondria 24 are intact. FIGS. 5B & C show electron micrographs of prostate adenocarcinoma cells 20 at 1.5 and at 4 hours after treatment with a 1:40 dilution of p-LDL, respectively. FIGS. 5B & C show the formation of cytoplasmic blebs 26 and the disruption of mitochondria 24 which were virtually converted to vacuoles 28. P-LDL was also used to kill Colo205, a colon adenocarcinoma; HepG2, a hepatoblastoma; and "Alexander cells," a hepatocarcinoma line.

In comparing two pairs of malignant: "normal" cells for relative sensitivity to p-LDL toxicity, U937 cells, a transformed monocyte-like line was compared to a monocyte fraction, and mesothelioma cells were compared to mesothelial cells. The U937 cells were completely dead in 24 hours with a dose of p-LDL at 1:60 dilution, but the normal monocytes were more than 80% viable even at a dose of 1:10 dilution of p-LDL. A similar difference was observed for the second pair. Thus, there is a substantial difference in sensitivity which makes it possible to bolster the systemic level of p-LDL in a cancerous patient to fight cancer while not substantially injuring the patient.

Adriamycin (Ad) and other molecules of its class have long been used as chemotherapeutic agents effective against certain types of cancer. They also have been suspected of generating free-radicals. The mechanism for such action is unknown, but two possible mechanisms are shown below:

1)

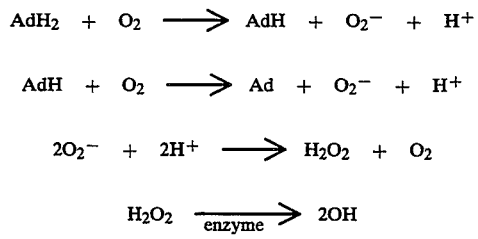

2)

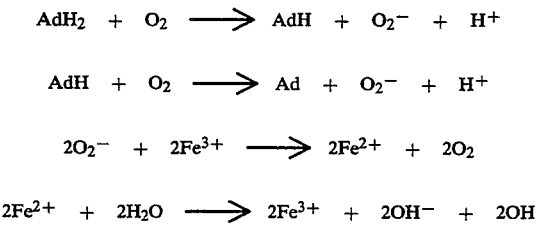

Other metal ions can substitute for $Fe^{3+}$. In accordance with the present invention, it is believed that adriamycin generates free radicals which in turn cause oxidation of lipoproteins.

EXAMPLE 1

Low density lipoprotein is obtained from Sigma Chemical, catalog no. L2139, or prepared from fresh human or animal plasma by standard methods. Lindren F. T., Silvers A., Jutagir R., Layshot L., Bradley D. D. Lipids 1977; 12: 278–282 and Lindren F. T., Adamson G. L., Jensen L. C., Wood P. D. Lipids 1975; 10: 750–756. Oxidized low density lipoprotein is prepared using either soluble horseradish peroxidase (Enzyme Commission Classification No. 1.11.1.7) or immobilized horseradish peroxidase as a catalyst. The immobilized enzyme has the advantage that it can be removed from the solution of oxidized low density lipoprotein before use. Each ml of low density lipoprotein solution (5 mg. protein per ml) is diluted with an equal volume of Dulbecco's phosphate buffered saline, and peroxidase of either form is added to a level of 800–1000 units per ml of solution. Following this, 0.1 ml of 3% hydrogen peroxide, $H_2O_2$, is added per ml of low density lipoprotein solution. The solution is maintained at room temperature and 0.1 ml of peroxide solution per ml low density lipoprotein solution is added each hour for two hours. A C-13 spectrum is obtained on the oxidized low density lipoprotein solution to determine the extent of lipid peroxidation as measured by the 128/130 ppm ratio. The preparation is stored at 2°–6° C.

EXAMPLE 2

Peroxidized low density lipoprotein is prepared by treating 5 mg of protein/ml human low density lipoprotein (as described in Example 1) with 2 mg/ml of horseradish peroxidase Type II. This is followed by the addition of 70 to 200 μliters of 3% hydrogen peroxide in one or two equal aliquots, the second addition being made several hours after the first addition. The peroxidation level is measured by the ratio of the intensity of the resonances at 128 and 130 ppm in the solution's carbon-13 NMR spectrum. A lower ratio indicates a reduction of the amount of polyunsaturated fatty acid side chains in the lipoprotein lipids. The 128/130 ppm ratio is typically greater than 0.9 before peroxidation and between 0.7 and 0.85 after peroxidation.

This technique can be employed with any lipoprotein. It is particularly desirable to peroxidize low density lipoproteins. Peroxidized low density lipoprotein, prepared by the aforementioned technique, was added to cultured cells at a variety of dilutions. The cultured cancerous cells were readily killed by the peroxidized low density lipoproteins.

EXAMPLE 3

Oxidized lipoproteins were prepared by reacting 8-methoxypsoralen with lipoprotein-containing plasma and ultraviolet light. 8-methoxypsoralen was added to two aliquots of plasma and those aliquots as well as two control aliquots were irradiated with the same type of light as that used by Edelson et al. The control plasma showed no change in the 128/130 ppm C-13 ratio following 30 minutes of ultraviolet A irradiation (the ratio was 0.98 before and 0.97 afterwards). However, the 8-methoxypsoralen containing plasma showed a reduction of the ratio from a pre-irradiation value of 0.98 to 0.77 following 30 minutes of light treatment. Thus, free-radical induced oxidation appears to occur and may be responsible for tile therapeutic effect observed by Edelson et al.

EXAMPLE 4

Oxidized lipoproteins were prepared by the addition of adriamycin to six aliquots of normal plasma and bubbling intermittently with 95% $O_2$:5% $CO_2$. An equal amount of adriamycin was also added to six additional aliquots of plasma and bubbled similarly with 95% $N_2$:5% $CO_2$. The ratio of the 128/130 ppm resonances changed as shown in the Table below. The lower ratio, as compared with the control sample indicates that peroxidation has occurred. Adriamycin mediated lipid peroxidation occurred in the presence of oxygen but not in its absence.

|  | 128/130 ppm intensity |
| --- | --- |
| Control plasma | 0.96 +/− 0.06 (n = 6) |
| Control plasma + Adriamycin + $O_2$ | 0.72 +/− 0.09 (n = 6) |
| Control plasma + Adriamycin + $N_2$ | 0.94 +/− 0.05 (n = 6) |

EXAMPLE 5

Once a patient is diagnosed as having cancer by methods well known in the art, a cholesterol lowering drug, such as lovastatin, is administered orally or intravenously to increase the number of low density lipoprotein receptors on the diseased cell membranes. Selectivity is based on the fact that malignant cells grow, divide and synthesize new membranes at a much greater rate than noncancerous cells and thus have a much greater intake of the cytotoxic low density lipoproteins. Lipoproteins are one source of fuel for a cell's metabolism. Taurine ($NH_2CH_2CH_2SO_3H$/ethanolamine-sulfonic acid) may also be used to increase the number of low density lipoprotein receptors on the diseased cell membranes.

EXAMPLE 6

Once a patient is diagnosed as having cancer by methods well known in the art, a cholesterol lowering drug, such as lovastatin, is administered orally or intravenously to increase the number of low density lipoprotein receptors on the diseased cell membranes. Selectivity is based on the fact that malignant cells grow, divide and synthesize new membranes at a much greater rate than noncancerous cells and thus have a much greater intake of the cytotoxic low density lipoproteins. Lipoproteins are one source of fuel for a cell's metabolism. Taurine ($NH_2CH_2CH_2SO_3H$/ethanolamine-sulfonic acid) may also be used to increase the number of low density lipoprotein receptors on the diseased cell membranes.

In addition, peroxidized low density lipoprotein is injected intravenously. The growth of the tumor is monitored by conventional methods and the peroxidized low density lipoprotein dose is adjusted accordingly.

EXAMPLE 7

Once a patient is diagnosed as having cancer by methods well known in the art, peroxidized low density lipoprotein is injected intravenously. The growth of the tumor is monitored by conventional methods and the peroxidized low density lipoprotein dose is adjusted accordingly.

EXAMPLE 8

Once a patient is diagnosed as having cancer by methods well know in the art, ditertiarybutyl peroxide is administered by i.v. (intravenous) injection. The growth of the tumor is monitored by conventional methods and tile ditertiary butyl peroxide dose adjusted accordingly. A cholesterol lowering drug, such as lovastatin, may also be injected intravenously to increase the number of low density lipoprotein receptors on the diseased cell membranes. Taurine ($NH_2CH_2CH_2SO_3H$/ethanolaminesulfonic acid) may also be used for this purpose.

The patient's blood oxygen supply may also be augmented by inhalation of elemental oxygen or by i.v. injection of perflurocarbon fluosal.

Additionally, the patient's supply of lipoproteins may be augmented by intravenous injection of lipoproteins enriched with triglycerides, phospholipids, or cholesterol esters.

The ditertiarybutyl peroxide of this procedure may be replaced with any of the following in its proper dose: riboflavin, peroxidase, lipoxidase, or other flavins, peroxides, organic peroxides or oxidases.

EXAMPLE 9

Once a patient is diagnosed as having cancer by methods well known in the art, an AV shunt or arterial bypass is attached to the patient. An extracorporeal peroxidizing module is attached to the AV shunt or arterial bypass. It has an inlet fluid connection from a pump which introduces hydrogen peroxide into the module which contains peroxidase or lipoxidase which peroxidizes the plasma lipoproteins in the presence of the hydrogen peroxide.

EXAMPLE 10

Once a patient is diagnosed as having malaria by methods well known in the art, a cholesterol lowering drug, such as lovastatin, is administered orally or intravenously to increase the number of low density lipoprotein receptors on the diseased cell membranes. Selectivity is based on the fact that malaria-infected cells have a higher metabolism rate than healthy cells and thus have a much greater intake of the cytotoxic low density lipoproteins. Lipoproteins are one source of fuel for a cell's metabolism. Taurine ($NH_2CH_2CH_2SO_3H$/ethanolamine-sulfonic acid) may also be used to increase the number of low density lipoprotein receptors on the diseased cell membranes. Table I below shows results of an experiment where over a 12 hour period malaria-infected red blood cells were treated with several different agents, in accordance with the present invention. Table I shows the cell count of treated cells as compared to the cell count of untreated cells.

TABLE I

| Agent | Live Parasite-Infected Cell Count |
| --- | --- |
| peroxide/peroxidase only | 12.4 |
| peroxide/peroxidase & bovine serum albumin | 12.9 |
| oxidized bovine serum albumin | 15.0 |
| oxidized LDL diluted 1:10 | 2.4 |
| oxidized HDL diluted 1:10 | 0.2 |
| phosphate buffered saline (untreated) | 11.6 |

EXAMPLE 11

Once a patient is diagnosed as having malaria by methods well known in the art, a cholesterol lowering drug, such as lovastatin, is administered orally or intravenously to increase the number of low density lipoprotein receptors on the diseased cell membranes. Selectivity is based on the fact that malaria-infected cells have a higher metabolism rate than healthy cells and thus have a much greater intake of the cytotoxic low density lipoproteins. Lipoproteins are one source of fuel for a cell's metabolism. Taurine ($NH_2CH_2CH_2SO_3H$/ethanolamine-sulfonic acid) may also be used to increase the number of low density lipoprotein receptors on the diseased cell membranes.

In addition, peroxidized low density lipoprotein is injected intravenously. The progress of the malaria infection is monitored by conventional methods and the peroxidized low density lipoprotein dose is adjusted accordingly. The extent of lipid peroxidation is measured by performing a proton and carbon-13 (128/130 ppm ratio) NMR analysis of the oxidized low density lipoprotein solution.

EXAMPLE 12

Once a patient is diagnosed as having malaria by methods well known in the art, peroxidized low density lipoprotein is administered orally or intravenously. The progress of the malaria infection is monitored by conventional methods and tile peroxidized low density lipoprotein dose is adjusted accordingly.

EXAMPLE 13

Once a patient is diagnosed as having malaria by methods well know in the art, ditertiarybutyl peroxide is administered by i.v. (intravenous) injection. The progress of the malaria infection is monitored by conventional methods and the ditertiarybutyl peroxide dose adjusted accordingly. A cholesterol lowering drug, such as lovastatin, may also be administered orally or intravenously to increase the number of low density lipoprotein receptors on the diseased cell membranes. Taurine ($NH_2CH_2CH_2SO_3H$/ethanolaminesulfonic acid) may also be used for this purpose.

The patient's blood oxygen supply may also be augmented by inhalation of elemental oxygen or by i.v. injection of perflurocarbon fluosal.

Additionally, the patient's supply of lipoproteins may be augmented by intravenous injection of lipoproteins enriched with triglycerides, phospholipids, or cholesterol esters.

The ditertiarybutyl peroxide of this procedure may be replaced with any of the following in its proper dose: riboflavin, peroxidase, lipoxidase, or other flavins, peroxides, organic peroxides or oxidases. The extent of lipid peroxidation is measured by performing a proton and carbon-13 (128/130 ppm ratio) NMR analysis of the oxidized low density lipoprotein-containing blood.

EXAMPLE 14

Once a patient is diagnosed as having malaria by methods well known in the art, an AV shunt or arterial bypass is attached to the patient. An extracorporeal peroxidizing module is attached to the AV shunt or arterial bypass. It has an inlet fluid connection from a pump which introduces hydrogen peroxide into the module which contains peroxidase or lipoxidase which peroxidizes the plasma lipoproteins in the presence of the hydrogen peroxide.

EXAMPLE 15

Once a patient is diagnosed as having a virus infection such as AIDS by methods well known in the art, peroxidized lipoproteins are injected intravenously. The progress of the HIV infection is monitored by conventional methods and the peroxidized low density lipoprotein dose is adjusted accordingly. The extent of lipid peroxidation is measured by performing a proton and carbon-13 (128/130 ppm ratio) NMR analysis of the oxidized low density lipoprotein solution.

The effect of oxidized LDL on HIV-infected cells was tested in an independent laboratory with the following results. CR10 cells chronically infected with HIV-1/NIT Virus and Phytohemagglutinin stimulated cultured peripheral blood mononuclear cells from individuals negative for HIV-1 antibody were incubated with an oxidized form of LDL. After 48 hours of incubation, exclusion assays were performed to determine cell survival following treatment with LDL. The Trypan Blue Exclusion assay results show that oxidized LDL has a selectively toxic effect on HIV-1 infected cells. See Table I below for specific test results.

TABLE I

| | | Viability as Deteremined by Trypan Blue Exclusion | |
|---|---|---|---|
| Day | Treatment | Uninfected Cells | Infected Cells |
| 0 | untreated | 89% | 90% |
| 2 | untreated | 89% | 87% |
| 2 | w/1:1000 p-LDL | 75% | 16% |

Whereas the above results have demonstrated that p-LDL is preferentially cytotoxic to HIV-infected cells, the results in Table II (below) show that pLDL treatment kills the HIV virus as well.

TABLE II

| HIV Antigen Endpoint Titration Results | | | |
|---|---|---|---|
| pLDL Dilution | CR10 Infected/ Treated Day 2 | pLDL Dilution | CR10 Infected/ Untreated Day 2 |
| 1:10 | 1:16 | untreated | 1:64 |
| 1:100 | 1:32 | | |
| 1:1000 | 1:32 | | |
| 1:10,000 | 1:32 | | |
| 1:100,000 | 1:32 | | |

Table II shows the titration results for HIV-1 antigen in CR10 culture supernatant fluids at Day 2 of treatment. This antibody-antigen precipitation experiment is designed using a titration dilution. In the infected and untreated controls the titration ratio was carried out to 1:64 to eliminate the antibody-antigen response. In the supernatant for the infected and treated cells, the titration ratio only needed to reach 1:16 for pLDL dilution of 1:10 and 1:32 for more dilute pLDL.

This experiment demonstrates that the HIV virus was less viable after treatment in comparison with controls. It is not yet known whether pLDL directly killed the virus or whether pLDL killed the host cell without which the virus cannot live, or both.

EXAMPLE 16

Once a patient is diagnosed as having AIDS or believed to be at risk for AIDS, by methods well known in the art, peroxidized low density lipoprotein is administered orally or intravenously. The progress of the HIV infection is monitored by conventional methods and the peroxidized low density lipoprotein dose is adjusted accordingly.

EXAMPLE 17

Once a patient is diagnosed as having AIDS or believed to be at risk for AIDS, by methods well known in the art, ditertiarybutyl peroxide is administered by i.v. (intravenous) injection. The progress of the HIV infection is monitored by conventional methods and the ditertiarybutyl peroxide dose adjusted accordingly.

The patient's blood oxygen supply may also be augmented by inhalation of elemental oxygen or by i.v. injection of perflurocarbon fluosal.

Additionally, the patient's supply of lipoproteins may be augmented by intravenous injection of lipoproteins enriched with triglycerides, phospholipids or cholesterol esters.

The ditertiarybutyl peroxide of this procedure may be replaced with any of the following in its proper dose: riboflavin, peroxidase, lipoxidase or other flavins, peroxides, organic peroxides or oxidases. The extent of lipid peroxidation is measured by performing a proton and carbon-13 (128/130 ppm ratio) NMR analysis of the oxidized low density lipoprotein-containing blood.

EXAMPLE 18

Once a patient is diagnosed or suspected as having a viral infection such as AIDS by methods well known in the art, an AV shunt or arterial bypass is attached to the patient. An extracorporeal peroxidizing module is attached to the AV shunt or arterial bypass. It has an inlet fluid connection from a pump which introduces hydrogen peroxide into the module which contains peroxidase or lipoxidase which in turn peroxidizes the plasma lipoproteins.

EXAMPLE 19

Once a patient is diagnosed as having a disease state characterized by diseased cells with an increased number of lipoprotein receptors or an enhanced ability to take-up lipoproteins, such as cancer, malaria and AIDS, by methods well known in the art, a supply of blood is secured. The blood supply source may be the diseased patient, a donor, a blood bank, or any other compatible blood supply source. Blood from sources other than the diseased patient have the advantage of being from a theoretically healthy individual.

The lipoproteins of the blood supply are then oxidized by adding an oxidant to the blood, thus producing of oxidized lipoproteins. A second approach to increasing the blood's level of oxidized lipoproteins involves adding oxidized lipoproteins to the blood. As a third approach, the first two approaches may be combined; that is, an oxidant as well as oxidized lipoproteins are added to the same blood supply.

When a blood supply other than the patient's is involved, the oxidized lipoprotein-containing blood may be stored until used. When the patient's blood is used, it may be reintroduced to the patient at the most advantageous time for treatment.

Several additional and optional treatment steps may be combined with the above-described procedure. They are as follows.

The oxygen available in the blood may be further increased by adding elemental oxygen or perflurocarbon fluosal to the blood.

The lipoprotein content of the blood could also be augmented by adding lipoproteins enriched with triglycerides, phospholipids, or cholesterol esters.

A chemotherapeutic effector agent may be added to the blood to further increase the number of lipoprotein receptors on the diseased cells or to further enhance the diseased cells' ability to take-up lipoproteins. Taurine and lovastatin are examples of such agents.

This treatment approach appears to work best when the lipoproteins referred to throughout the procedure are low density lipoproteins.

EXAMPLE 20

One embodiment of this invention involves providing a blood supply which may include the diseased patient's blood, a blood bank, or any other compatible blood supply.

Figure 10:
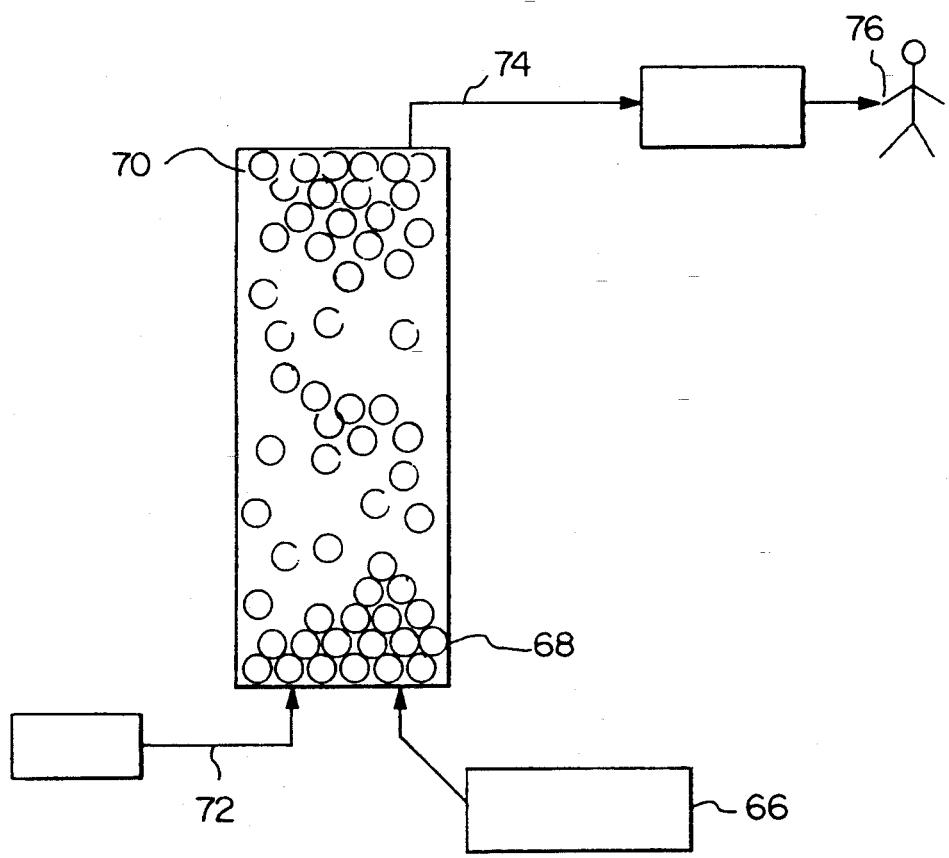
FIG. 10 shows a further embodiment of the apparatus for oxidizing the lipoproteins in a blood supply.

Heparinized blood 66 is added to the bottom of a container 68, shown in FIG. 10, the walls of which confine a source of an immobilized enzyme, such as horseradish peroxidase coated beads 70. Hydrogen peroxide 72 is introduced to the bottom of the container resulting in the formation of oxidized lipoproteins in the blood which exits from the top of the container. The oxidized lipoprotein-containing blood 74 is introduced to the patient 76 when treatment of the disease state is desired.

This procedure may be further enhanced by introducing an oxidant to the blood prior to administering it to the patient.

While the foregoing invention has been described with reference to its preferred embodiments, various alterations and modifications will occur to those skilled in the art. All such alternations and modifications are intended to fall within the scope of the appended claims.

What is claimed is:

1. A method for treating a disease state characterized by diseased cells with an increased number of lipoprotein receptors or an enhanced ability to take-up lipoproteins, which method comprises
    (a) supplying blood,
    (b) oxidizing the lipoproteins in the blood,
    (c) injecting the oxidized lipoprotein-containing blood of step (b) into the patient to be treated, and
    (d) administering a chemotherapeutic effector agent to further increase the number of lipoprotein receptors on said diseased cells
wherein said chemotherapeutic effector agent is taurine or lovastatin.

2. A method for treating a disease state characterized by diseased cells with an increased number of lipoprotein receptors or an enhanced ability to take-up lipoproteins, which method comprises
    (a) supplying blood,
    (b) adding oxidized lipoproteins to the blood,
    (c) injecting the oxidized lipoprotein-containing blood of step (b) into the patient to be treated, and
    (d) administering a chemotherapeutic effector agent to further increase the number of lipoprotein receptors on said diseased cells
wherein said chemotherapeutic effector agent is taurine or lovastatin.

3. A method for treating a disease state characterized by diseased cells with an increased number of lipoprotein receptors or an enhanced ability to take-up lipoproteins, which method comprises
    (a) withdrawing blood from a patient,
    (b) oxidizing the lipoproteins in the blood,
    (c) reinjecting the oxidized lipoprotein-containing blood of step (b) into the patient to be treated, and
    (d) administering a chemotherapeutic effector agent to further increase the number of lipoprotein receptors on said diseased cells
wherein said chemotherapeutic effector agent is taurine or lovastatin.

4. A method for treating a disease state characterized by diseased cells with an increased number of lipoprotein receptors or an enhanced ability to take-up lipoproteins, which method comprises
    (a) withdrawing blood from a patient,
    (b) adding oxidized lipoproteins to the blood,
    (c) reinjecting the oxidized lipoprotein-containing blood of step (b) into the patient to be treated, and
    (d) administering a chemotherapeutic effector agent to further increase the number of lipoprotein receptors on said diseased cells
wherein said chemotherapeutic effector agent is taurine or lovastatin.

5. A method for treating a disease state characterized by diseased cells with an increased number of lipoprotein receptors or an enhanced ability to take-up lipoproteins, which method comprises (a) detecting the disease state,
(b) administering oxidized lipoproteins to the patient, said oxidized lipoproteins increasing the quantity of oxidized lipoprotein taken up by the diseased cells thereby leading to the destruction of the diseased cells, and
(c) administering a chemotherapeutic effector agent to further increase the number of lipoprotein receptors on said diseased cells
wherein said chemotherapeutic effector agent is taurine or lovastatin.

* * * * *